(12) United States Patent
Tsyrulnykov

(10) Patent No.: US 9,364,603 B2
(45) Date of Patent: Jun. 14, 2016

(54) MULTIPLE LAYER DILATOR SINGLE POINT VASCULAR ACCESS DEVICE

(71) Applicant: Eduard Tsyrulnykov, Mequon, WI (US)

(72) Inventor: Eduard Tsyrulnykov, Mequon, WI (US)

(*) Notice: Subject to any disclaimer, the term of this patent is extended or adjusted under 35 U.S.C. 154(b) by 32 days.

(21) Appl. No.: 14/310,373

(22) Filed: Jun. 20, 2014

(65) Prior Publication Data

US 2014/0378893 A1 Dec. 25, 2014

Related U.S. Application Data

(60) Provisional application No. 61/837,891, filed on Jun. 21, 2013.

(51) Int. Cl.
*A61M 1/00* (2006.01)
*A61M 1/36* (2006.01)
*A61M 29/00* (2006.01)

(52) U.S. Cl.
CPC .............. *A61M 1/3661* (2014.02); *A61M 29/00* (2013.01)

(58) Field of Classification Search
CPC ....... A61M 1/14; A61M 1/30; A61M 1/3661; A61M 29/00
USPC .......................................... 604/28, 4.01, 6.05
See application file for complete search history.

(56) References Cited

U.S. PATENT DOCUMENTS

| 4,149,535 | A | * | 4/1979 | Volder | A61M 5/1582 604/164.01 |
|---|---|---|---|---|---|
| 4,629,450 | A | | 12/1986 | Suzuki et al. | |
| 4,722,725 | A | | 2/1988 | Sawyer et al. | |
| 4,832,684 | A | * | 5/1989 | Popovich | A61M 1/287 604/28 |
| 5,156,596 | A | | 10/1992 | Balbierz et al. | |
| 5,250,038 | A | | 10/1993 | Melker et al. | |
| 5,380,290 | A | | 1/1995 | Makower et al. | |
| 6,132,405 | A | * | 10/2000 | Nilsson | A61M 1/285 604/264 |
| 6,824,553 | B1 | | 11/2004 | Samson et al. | |
| 7,025,746 | B2 | | 4/2006 | Tal | |
| 7,976,542 | B1 | | 7/2011 | Cosman et al. | |
| 8,226,633 | B2 | | 7/2012 | Markel et al. | |
| 8,241,245 | B2 | | 8/2012 | Markel et al. | |
| 2003/0153874 | A1 | * | 8/2003 | Tal | A61M 25/0606 604/164.1 |
| 2005/0090802 | A1 | | 4/2005 | Connors et al. | |
| 2007/0239033 | A1 | * | 10/2007 | Tearney | A61B 5/0059 600/476 |
| 2009/0312687 | A1 | * | 12/2009 | DeFonzo | A61M 25/003 604/6.16 |
| 2011/0130745 | A1 | * | 6/2011 | Shevgoor | A61M 5/14 604/523 |
| 2013/0150767 | A1 | | 6/2013 | Tsyrulnykov et al. | |

FOREIGN PATENT DOCUMENTS

WO WO-2014-205341 12/2014

* cited by examiner

*Primary Examiner* — Edelmira Bosques
*Assistant Examiner* — Leah Swanson
(74) *Attorney, Agent, or Firm* — Jonathan M. Rixen; Lemaire Patent Law Firm, P.L.L.C.

(57) ABSTRACT

Single needle vascular access systems, devices and methods for use in hemodialysis and apheresis procedures the device includes a multi-layer dilator. A single needle vascular access device includes a body having a venous and arterial passage with both in fluid communication with a vascular dilator. A cannulation needle is guided through the arterial passage and vascular dilator to cannulate a graft or fistula. Following cannulation, the dilator is gently introduced into the vessel. The cannulation needle is removed, and a venous tube is introduced through the venous passageway through the vascular dilator and into the fistula or graft. Blood is then removed from the body through the vascular dilator side orifices and returned through the venous line.

20 Claims, 9 Drawing Sheets

SECTION VIEW A-A

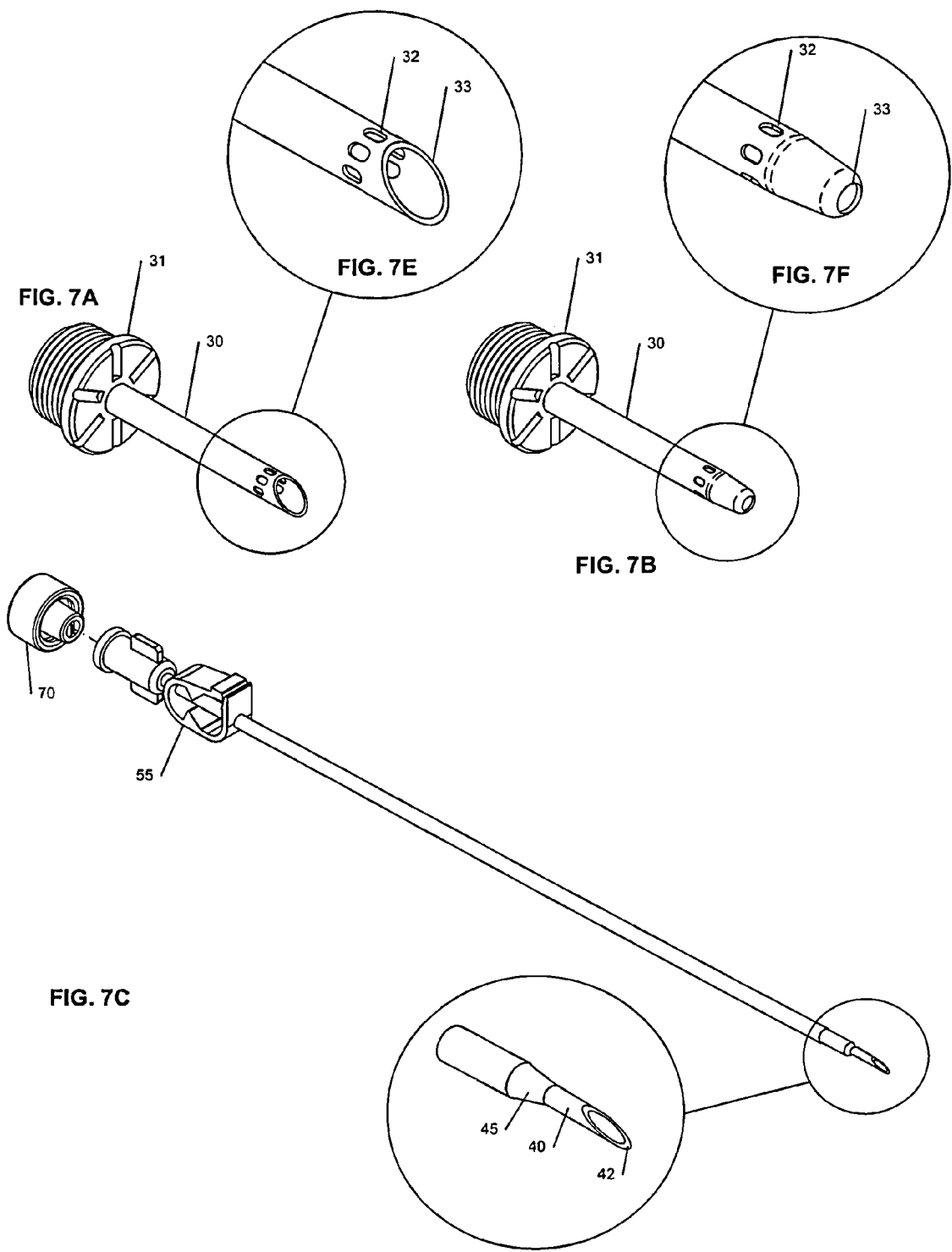

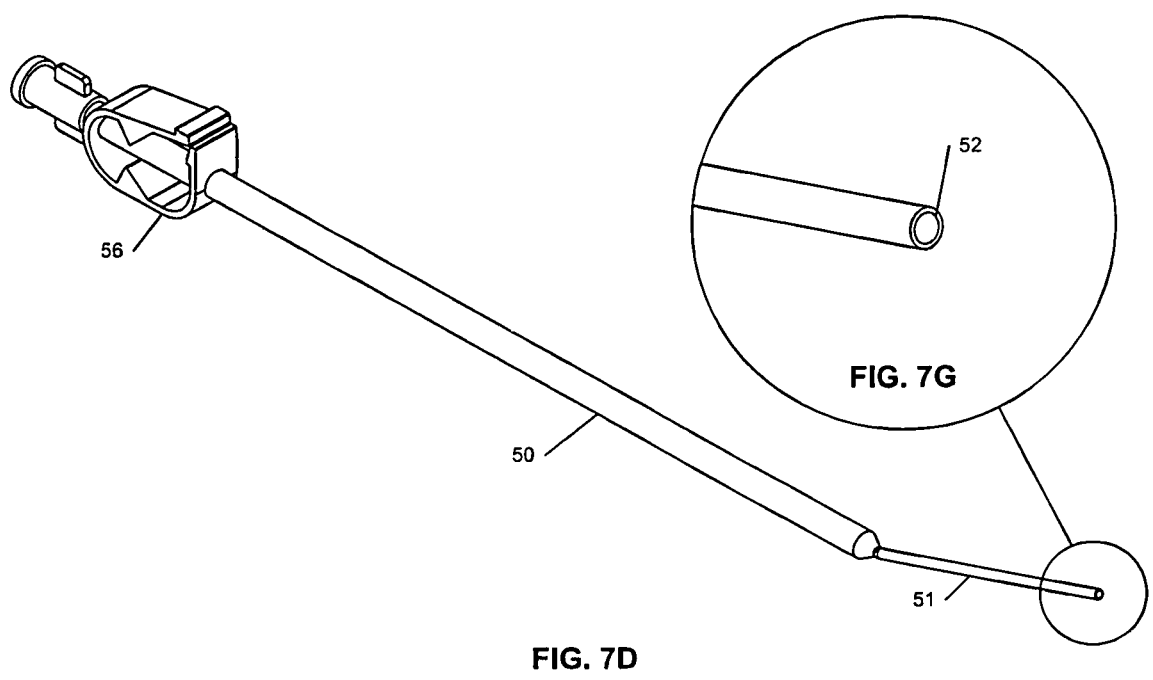

MULTIPLE LAYER DILATOR SINGLE POINT VASCULAR ACCESS DEVICE

BACKGROUND

1. Technical Field

The invention relates to methods and devices to facilitate bi-directional blood flow through a single access point. More particularly the invention relates to extracorporeal hemodialysis of a patient's blood with a single cannulation even in patients having difficult sites to access.

2. Description of the Related Art

Historically, kidney diseases have been of critical concern to human life. Many kinds of kidney diseases interfere with the function of the kidney such that the kidney ceases to remove waste and excess water from the blood. When the kidney is sufficiently impaired that large portions of the waste products and water are not removed from the blood, the life of the patient cannot be preserved unless a way is provided for artificially performing the function of the impaired kidney. Even today, the same general procedure is used for dialyzing patients' blood that was used very early in the treatment of kidney disease.

For example, the most commonly accepted practice for dialyzing a patient's blood extracorporeally requires the surgical creation of a vascular access such as arterio-venous fistula (artificial connection between artery and using the native vein) or graft. Grafts are much like fistulas in most respects, except that an artificial vessel is used to join the artery and vein. The graft usually is made of a synthetic material, often PTFE, but sometimes chemically treated, sterilized veins from animals are used. Grafts are inserted when the patient's native vasculature does not permit a fistula.

Sufficient blood flow for dialysis is then obtainable by cannulation of fistula or graft with large bore needles. Normally, two hollow needles are used to perform two cannulation on the patient hemodialysis access (fistula or graft) so that two point blood-communication sites exist simultaneously in the patient. Conventionally, blood is withdrawn from one part of the punctured hemodialysis access, forced through a hemodialyzer and thereafter forced into the remaining part of the hemodialysis access. The needles have to be substantially distant from one another to prevent recirculation of blood between the access sites.

It is well-known that the life expectation and effective function of a hemodialysis access is inversely related to the number of cannulations. Tissue repeatedly subjected to the trauma of cannulation is much more susceptible to inflammation and neointimal hyperplasia, thrombosis and pseudo aneurism development. Such trauma may result in destruction of the graft or fistula triggering a requirement for another expensive operating procedure to replace the graft or fistula so that routine treatment may be resumed.

Systems for hemodialysis access to a fistula or graft cannulation can generally be divided on the following groups.

Two Needle Cannulation

Two needle cannulation procedures are well known being the first developed and the most widely used s at the present time. They are able to provide flow high flow rates of up to 600 ml/minute to minimize patient clinical procedure time and provide the best nitrogen and creatinine clearance/removal from the body. The disadvantages of these systems compared to a single cannulation approach, include pain and trauma to access, the risk for developing complications including pseudoaneurysm, prolonged post treatment bleeding, outflow stenosis and the presence of matured vascular access. In addition, the preferred placing of two needles at least 12 mm apart from each other which cannot be achieved at least at 30% of all newly placed accesses (so called failure or non-maturation of vascular access), An example of two needle cannulation can be found at the website of Baxter.

Sequential Flow Single Needle Cannulation

A sequential flow single needle cannulation system uses a single needle cannulation for both removing and replacing blood by alternating between forward and reverse flow through the single needle. The benefits of this system are that the one needle cannulation decreases trauma and pain in the area of the cannulation since only one cannulation is required. A disadvantage is that the high recirculation rate results in extensive remixing of treated and untreated blood, which reduces the effectiveness of the dialysis procedure. An example of this approach is disclosed in U.S. Pat. No. 4,940,455.

Telescoping One Needle Cannulation

Another single needle system including a one needle cannulation uses dual coaxial tubes to form an integral 2 lumen needle to simultaneously add and remove a patient's blood with one introduction point. The benefit of this system is that only one needle cannulation is required thereby decreasing the trauma/pain in the area of cannulation. The disadvantages of this procedure include that using a large sized (usually 14 gauge) cannulation needle as an outer tube (without using a single or double dilator) which restricts blood flow through the system to an average flow of 300-400 ml/minute. These low flow rates are not acceptable for the most hemodialysis patients and not preferred by the care providers. Furthermore, using a rigid inner tube material makes the device inappropriate to use in difficult geometry access such as stenotic, snail, torturous and angled fistula. An example of this system is the OneSite® system from NxStage® Medical, Inc.

SUMMARY OF THE INVENTION

Devices, systems and methods are provided for a single needle vascular access device for routine use in hemodialysis and apheresis procedures using a single access point. The vascular access device includes a body having a venous passageway for blood returning to the patient from a hemodialysis unit machine and an arterial passageway for receiving the patient's blood all in fluid communication with a multilayered vascular dilator. The device can be operated in any orientation. For example, the arterial passageway and the venous passageway may be vertical stacked above each other, or horizontally positioned parallel to each other. The arterial passageway is substantially straight linear through the body of the device to allow insertion and withdrawal of the retractable cannulation needle which is connected/attached to the internal dilator and after cannulation and securing the device inside the access and then passing blood from the vascular access to the hemodialysis machine. An external/back end of the arterial passageway is provided with a small bore adapter to connect the device to the arterial end of standard hemodialysis lines. The venous passageway intersects the arterial passageway as a side branch, forming a Y or V shape within the body. The angle between the venous and arterial passageway less than 30 degrees and preferably about 15 degrees helps minimize the pressure drop and eliminate tube constriction at the ben. The venous passageway is sized to allow insertion of the venous tube for replacing processed blood to the patient. A venous passageway external end is provided with a large bore adapter which may be of a variety of configurations such as a friction fit, or push and click style to secure the venous tube and prevent leakage of air or blood.

An external vascular dilator is removably fastened to the body of the device and is located at or near the intersection of the venous passageway with the arterial passage. The internal dimensions of the external vascular dilator are sized to sequentially receive the cannulation needle, an internal dilator and later after cannulation and securing the device inside the vascular access has been completed, the venous tube tip narrow segment. The external vascular dilator distal end has an open tip to allow the retractable internal dilator, and the retractable cannulation needle, preferably 17 or 18 gauge, to pass through and access the fistula or graft without any gap between the cannulation needle, internal dilator and the external vascular dilator. There is a smooth, seamless transitioning between the cannulation needle, the internal dilator and the external vascular dilator. The front opening of the external dilator is preferably sized to allow the cannulation needle connected to the internal dilator to pass freely without any excess space to allow solid material to collect during the cannulation process. The external vascular dilator tip and the internal dilator tips are blunt or rounded to stretch the opening created by the cannulation needle, without cutting or tearing the tissue. The external vascular dilator also has funneled side orifices to allow blood to enter the interior of the vascular dilator. To improve blood flow rates, preferably, the side orifices are funnel shaped having a sloped edge from an exterior surface to an interior surface. As such, this allows the use a larger size dilator even on a small (non-maturing) access without the risk of collapsing the wall of access under the influence of negative pressure, created by withdrawal of blood and prevents occluding the side orifices by the collapsed wall of the access. The diameter of the external vascular dilator, the number and characteristics of the side orifices are among the parameters that may be varied depending upon the desired blood flow rate, depth of access, its size and the allowed degree of recirculation desired for the procedure are patient specific variable parameters.

A cannulation needle connected to the internal dilator is guided through the arterial passageway and the external vascular dilator to cannulate a graft or fistula.

It is well known that during the cannulation, skin and tissue could be pulled and held firmly while a long needle is inserted into the vascular access. After the needle and dilator are inserted, the skin and tissue are released. The needle track that forms during this procedure takes the shape of the letter "Z," which gives the procedure its name. This zigzag track line becomes self-sealing and prevents blood from leaking into surrounding tissue. With the present invention an improvement has been made resulting in a modified classical Z track technique. In the modified method, it has been discovered that pulling skin parallel to Langer lines in the area of cannulation provides much better and farther movement of skin and results in better hemostasis after the procedure, less pain during cannulation and minimizes insertion force for the procedure. This specific direction for pulling skin has not been found in the prior art for this procedure. It is very important to provide hemostasis during cannulation. By allowing the use of a small size of the needle (typically 17, 18, 18.5 gauge) an initially small size cannulation track is created. During the process of cannulation and insertion of the needle and the internal dilator and the external vascular dilator into the cannulation track is being dilated. Following needle insertion the two larger diameter dilator insertion compresses the cannulation track from inside for the whole period of dialysis and as a result minimizes bleeding from the cannulation track and the wall of the access.

After the cannulation needle perforates the skin and wall of the vascular access, the internal dilator and the vascular dilators are gently introduced into the fistula or graft. As soon as the external vascular dilator is positioned and secured inside the vascular access, the cannulation needle and the internal dilator are removed. A venous tube has a narrow end with an opening on its end. The venous tube narrow end is introduced through the external venous passageway through the external vascular dilator with non-linear movements and into the fistula or graft. The non-linear movement may include a combination of rotational and forward with occasional backward movement. Another example includes the modified Z-track injection technique described previously. The venous tube narrow end is then advanced approximately 4 to 5-mm beyond the vascular dilator tip.

By placing the funneled withdrawal side orifices in the dead zone, in the wall of the external vascular dilator (in contrast to the front opening for a conventional regular needle) and in addition, creating the higher flow rates then can be obtained with conventional systems decreases the chance for recirculation of blood between the withdrawal ports which are the vascular dilator side orifices and the internal venous tube tip. This process prevents blood recirculation even with the distance between withdrawal and return sites from 4.5-7 mm apart. For example, spectrophotometry results shows 0.2-3.2% of recirculation with a distance of 5 mm between the withdrawal and return sites and flow rate inside the fistula of 600 ml/min this distance is ideal for the failing, non-maturing, stenotic vascular access. The average blood flow rate inside the fistula is about 1000-1200 ml/min, which helps to minimize the chance for recirculation.

As the venous tube is freely rotatable within the body and the vascular dilator, the venous tube may be adjusted to the geometry of the particular access. Upon securing the external portion of the venous tube with the large bore adapter, blood is then removed from the patient through the external vascular dilator side orifices into the arterial passageway and sent through the arterial line connected to the arterial passageway for transfer to the hemodialysis machine. The patient's blood is then returned through the venous tube and discharged through the end orifice of the venous tube into the patient's blood stream.

OBJECTS OF THE INVENTION

It is a primary object of the present invention to provide an improved device using a small size needle with a multilayered dilator to provide mechanical compression of cannulation track and wall of the access from inside during hemodialysis procedure and resulting an improved hemostasis with only an average blood loss of 1 to 5-ml from the procedure and a decreased post treatment bleeding time and decreased pain during treatment.

It is another object of the present invention to provide an improved device using a multilayer dilator including at least an internal dilator that may cooperate with a variety of needles sizes, to provide a decreased insertion force.

It is another object of the present invention to provide an improved method using the modified Z track technique (pulling skin parallel to Langer lines in the area of cannulation providing better hemostasis after the procedure, less pain during cannulation and minimize insertion force during the procedure.

It is another object of the present invention to provide an improved device using multiple funneled side holes allow us to use large size external vascular dilator even for small fistulas and grafts (with internal diameter about 4 mm) without risk that collapsed wall of vascular access will occlude withdrawal from the side orifice.

It is another object of the present invention to provide an improved method placing withdrawal side orifices in the dead zone (not tip of the tube) to prevent recirculation of blood with the distance between tip of internal hole and withdrawal side orifices between 4.5-7 mm which will be ideal for failing/non maturing/stenotic fistulas It is another object of the present invention to provide a device having the location of withdrawal side orifices will be determined by the depth of the vascular access and desired coefficient of recirculation.

It is another object of the present invention to provide an improved method of extracorporeal hemodialysis using a single cannulation for each treatment.

It is another object of the present invention to provide a single entry needle to reduced damage to a graft or fistula.

It is yet a further object of the present invention to provide a single access dialysis needle having two lumens and a volume capacity at or above 600-700 ml/min for blood removal without using large needles (14 gauges) for cannulation.

It is yet a further object of the present invention to provide a procedure to reduce patient time in clinical treatment.

It is yet a further object of the present invention to provide a small diameter cannulation needle to reduce patient pain It is yet a further object of the present invention to provide a small diameter cannulation needle to reduce damage to graft or fistula.

It is yet a further object of the present invention to provide an external dilator that could be revolved/flipped inside vascular access to achieve better position for blood exchange without risk of damaging inner layer of the graft/endothelium of fistula. Currently, because of the risk of damaging the vascular access by sharp portions of the needle which is not removed during blood withdrawal, rotating of needles is not recommended by the National Kidney Foundation. As the present invention does not have sharp parts inside the vascular access during hemodialysis, the vascular dilator can be safely rotated after cannulation needle with attached internal dilator is removed.

It is yet a further object of the present invention to provide a rotatable venous tube to assist threading into a vessel with having a tortuous path such as a tortuous fistula, snail fistula or difficult geometry fistula.

It is yet a further object of the present invention to provide a ring or marker band locatable by standard instrumentation at or near the venous tube tip.

It is yet a further object of the present invention to provide larger diameter dilator tubes to be used as a part of a device or simultaneously in combination with standard dialysis needles and connecting for two needle systems.

It is yet a further object of the present invention to provide larger diameter venous tubes.

It is yet a further object of the present invention to provide a high blood flow rate.

It is yet a further object of the present invention to minimize pressure in venous segment of the system, which is contributing factor in developing of stenosis of hemodialysis access.

It is yet a further object of the present invention to provide a multilayered vascular dilator that will distend the wall of the graft or fistula after cannulation without resulting in additional trauma, bleeding or pain.

It is yet a further object of the present invention to provide a device that may utilize an internal multilayered dilator that will distend tissue of graft or fistula after cannulation without causing additional trauma, bleeding or pain.

It is yet a further object of the present invention to provide a device that may simultaneously utilize more than one concentrical/coaxial internal dilator that will distend tissue of graft or fistula after cannulation without causing additional trauma, bleeding or pain.

These and other objects and features of the present invention will become more fully apparent from the description below.

BRIEF DESCRIPTION OF THE DRAWINGS

FIG. 7A provides a view of the external vascular dilator with side orifices on cannula wall.

FIG. 7B provides a view of an alternate embodiment of the external vascular dilator.

FIG. 7C provides a view of the cannulation needle with the blood flow detector.

FIG. 7D provides a perspective view of the venous tube.

FIG. 7E provides a detail view of the external vascular dilator with a beveled end.

FIG. 7F provides a detail view of the external vascular dilator end with a rounded end using the annular space as a conduit for blood withdrawal.

FIG. 7G provides a detail view of the venous tube end.

DETAILED DESCRIPTION OF EXEMPLARY EMBODIMENTS

Figure 1:
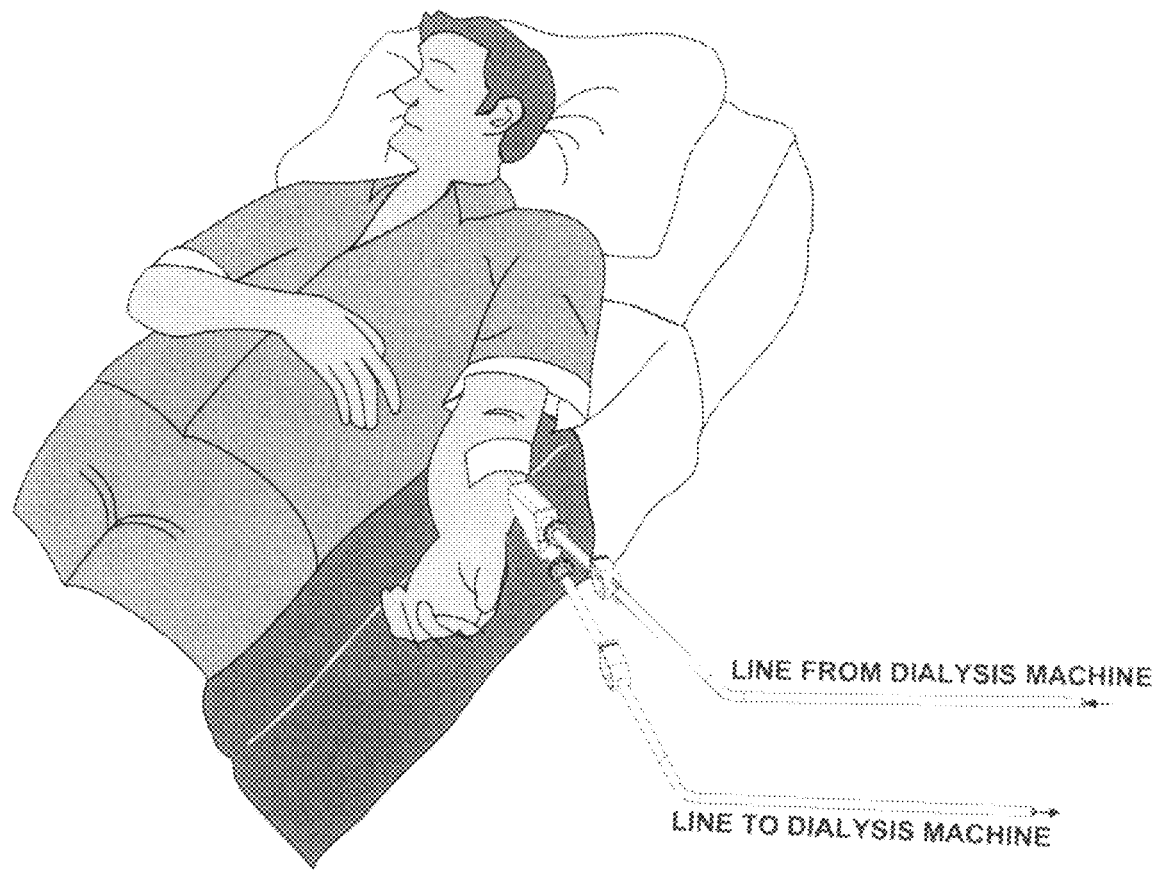
FIG. 1 provides a perspective view of the device in place on a patients arm during dialysis.
Figure 2A:
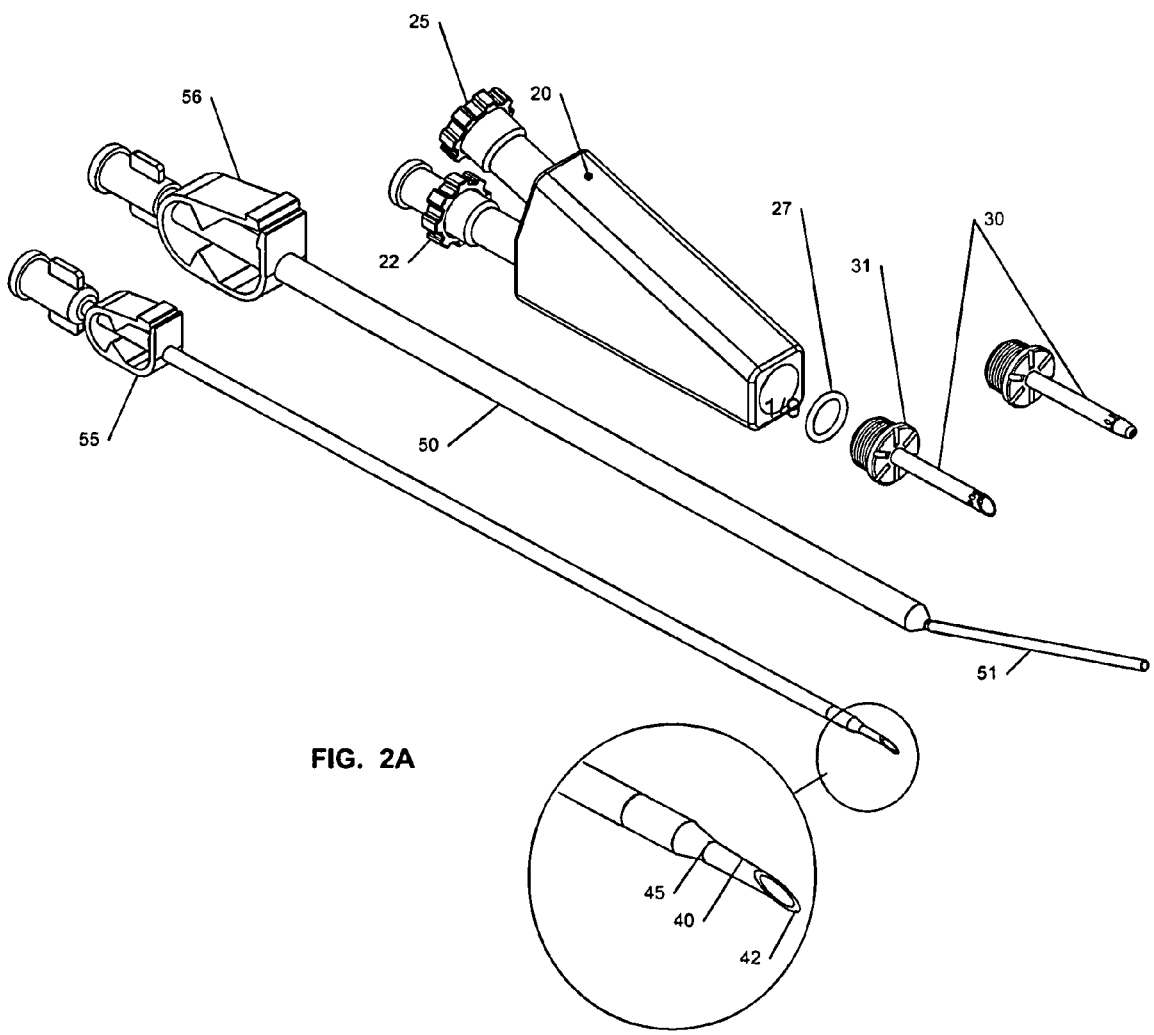
FIG. 2A provides a perspective view of the body with its associated parts.
Figure 2B:
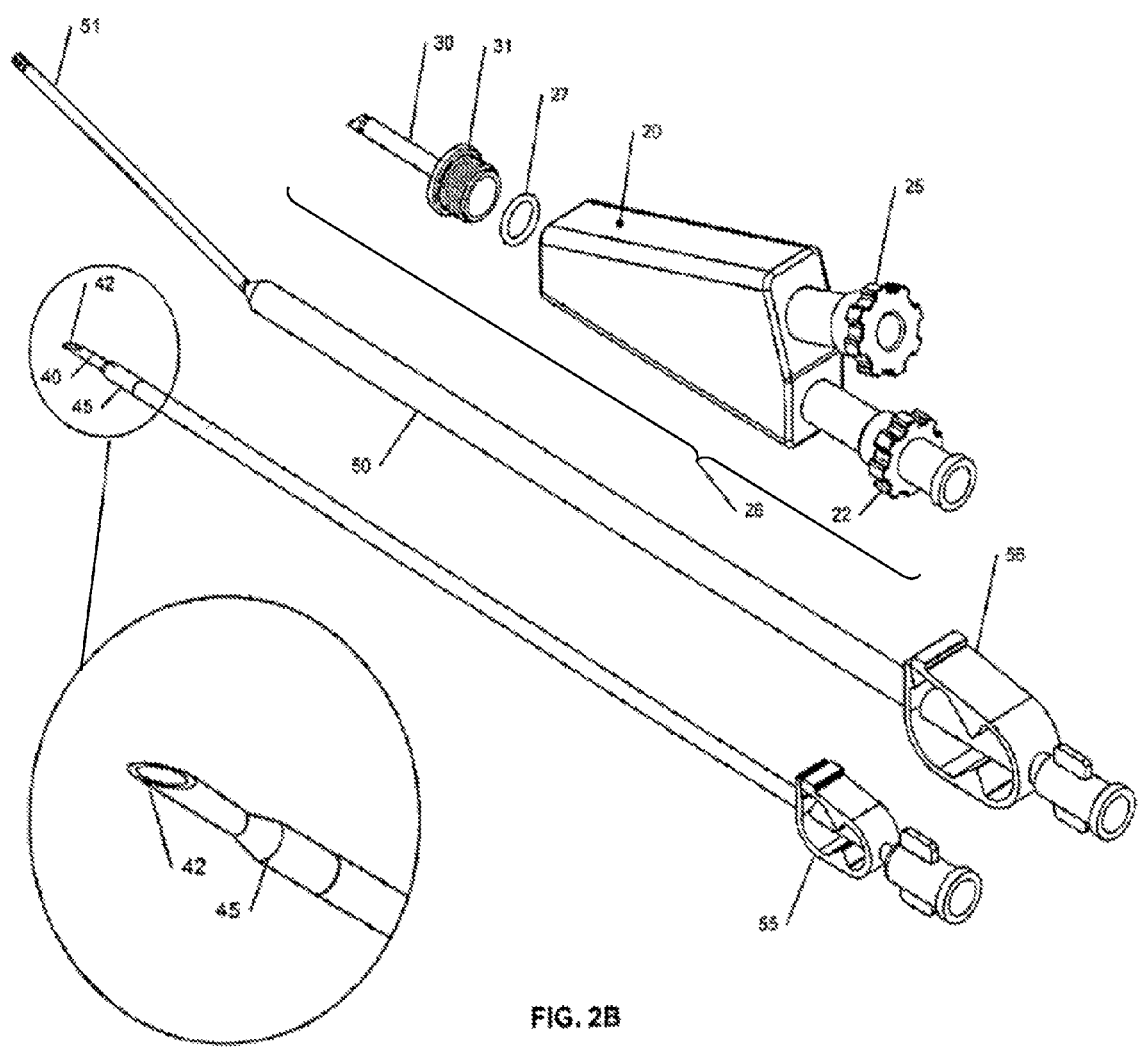
FIG. 2B provides another perspective view of the body.
Figure 3A:
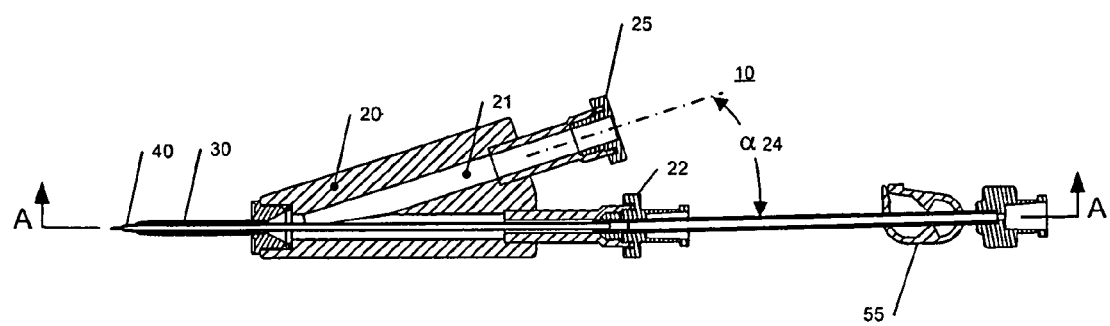
FIG. 3A provides a side view of the body with the cannulation needle installed.
Figure 3B:
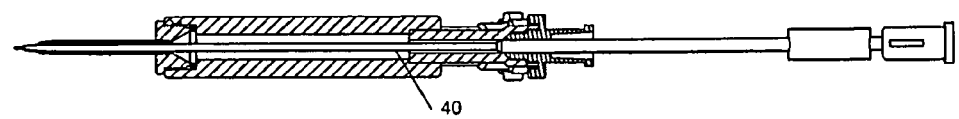
FIG. 3B provides a detail of a cross-sectional view of the body showing the securing screw.
Figure 4:
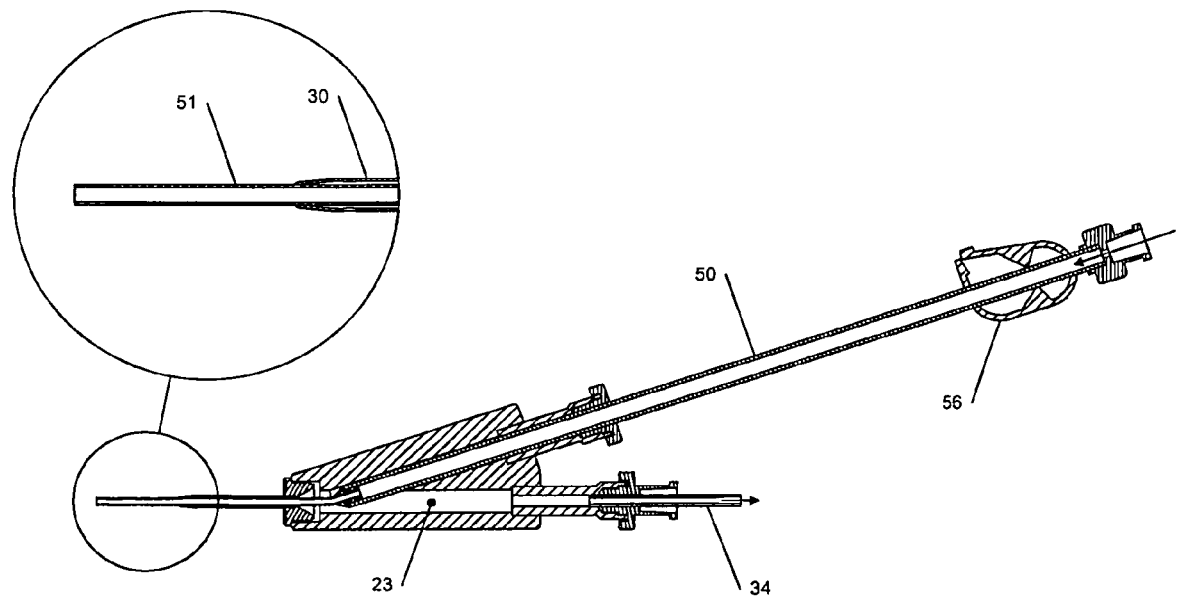
FIG. 4 provides a side view with the venous tube in place.
Figure 5:
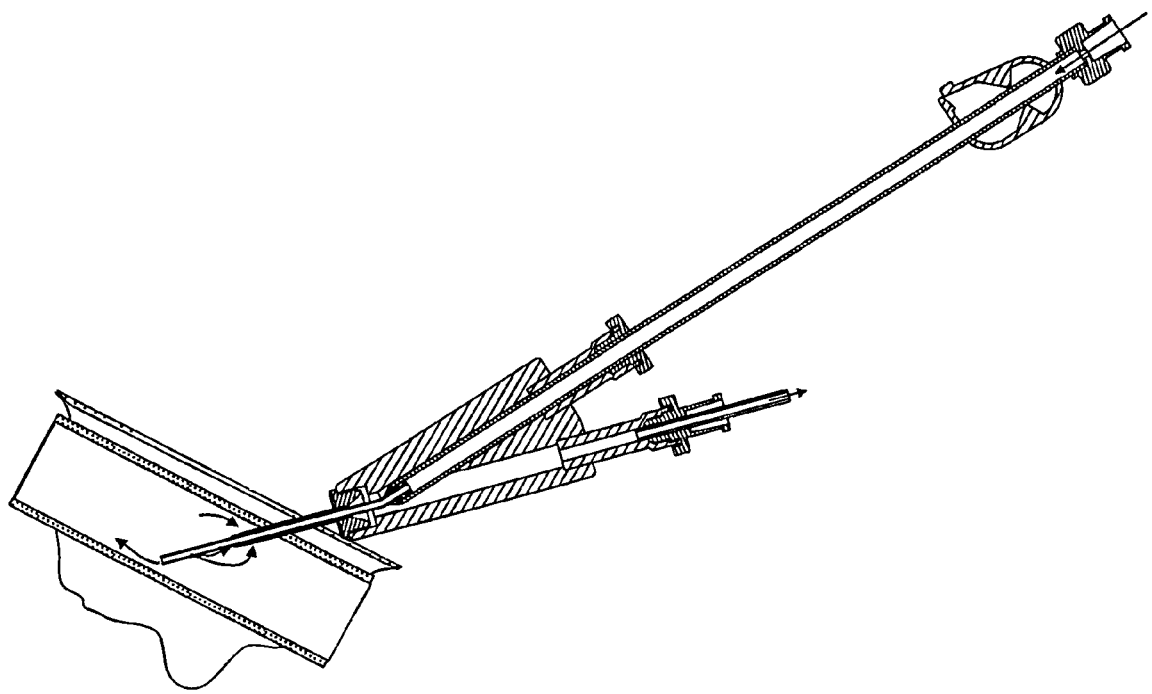
FIG. 5 provides a cross-section of the device inside the hemodialysis access with venous tube installed.
Figure 6:
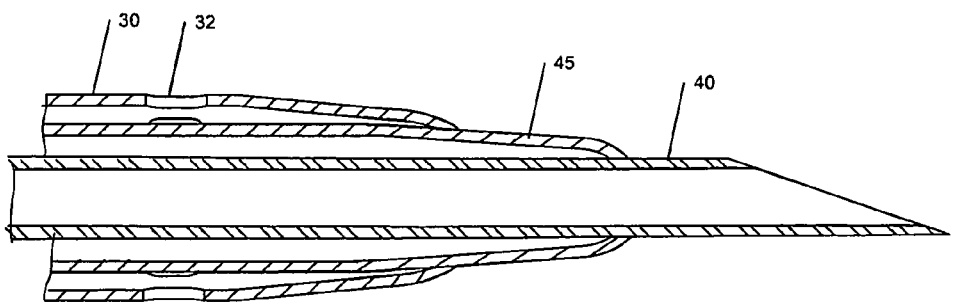
FIG. 6 provides a cross-section of the vascular dilator with the cannulation needle installed.

The vascular access device 10 is shown situated on a patient's arm in FIGS. 1 through 4. With reference to FIG. 1, the vascular access device 10 includes a body 20 having a venous passageway 21 and arterial passageway 23 in fluid communication with an external vascular dilator 30 also termed vascular dilator as this dilator is located on the external surface of the device. Assembly 26 includes body 20, small bore adapter 22, large bore adapter 25, O-ring 27, muzzle 31, and external vascular dilator 30. During use, the external vascular dilator 30 is generally positioned extending through the patients vessel wall, resulting in being partially external to the patient's vessel. The arterial passageway 23 is substantially straight linear through the body 20 to allow insertion and withdrawal of the cannulation needle 40 connected to the internal dilator 45 which, after being inserted through the patient's vessel wall and positioned for use is typically totally internal to the patient's vessel. An end of the arterial passageway 23 is provided with a small bore adapter 22. The small bore adapter 22 may be provided with a sealing adapter fitting such as a Luer taper fitting to connect to an arterial tube 34 to carry blood to the dialysis machine. The venous passageway 21 intersects the arterial passageway 23 as a side branch, forming a Y or V shape within the body 10. An angle alpha 24 is formed between junction of the venous and arterial passageway. It is an acute angle generally less than 30 degrees and preferably about 15 degrees. The small angle minimizes pressure drop at the intersection of the passageways and makes venous tube 50 easier to position. The venous passageway 21 is sized to allow insertion of the venous tube 50 for replacing processed blood to the patient. The distal end of the venous tube 50 may have a removable stopper to prevent movement of the venous tube inside the vascular access. A venous passageway proximal end is provided with a large bore adapter 25 to secure the venous tube 50. The terms small bore and large bore adapters are used to provide a seal between an instrument, catheter or tubing and the body 20. An example would be a Touhy Borst adapter. Any adapter providing substantially the same functionality may be considered for use.

A vascular dilator 30 proximal end is removably fastened to the body and is located at or near the intersection of the venous passageway 21 with the arterial passageway 23. The external vascular dilator 30 may be within a range of 2 to 16 french catheter size attached to a muzzle 31 at or substantially near the intersection of the venous and arterial passageways. The muzzle 31 is threaded to mate with corresponding threads on the body 20 front face. An O-ring 27 is provided between the muzzle 31 and the body 20 to provide a tight seal. In a single-use disposable embodiment of this device, the external vascular dilator 30 may be integral with body 20, eliminating the need of any threaded connections or O-ring. The external vascular dilator 30 is sized to sequentially receive the cannulation needle 40 attached to the internal dilator 45 and after cannulation, securing the device and removing the cannulation 40 and internal dilator 45, the venous tube 50. The external vascular dilator 30 has an open tip to allow the cannulation needle 40 with attached internal dilator 45 to pass freely without any excess space to allow solid material to collect. This is to prevent skin from sticking and/or jamming during cannulation. The vascular dilator tip 33 may be blunt or rounded to stretch the opening created by the cannulation needle 40, without cutting or tearing the tissue. The vascular dilator tip 33 may be beveled or rounded which could be used in a standard configuration or in a buttonhole technique cannulation in either configuration. The vascular dilator tip 33 may be tapered to a blunt or rounded end to stretch the opening created by the cannulation needle 40, without cutting or tearing the tissue.

The vascular tip 33 is beveled which can be used when the buttonhole technique cannulation is used to access the fistula or graft. The front opening of the external vascular dilator 30 is preferably sized to allow both the cannulation needle 40 and the internal dilator 45. The cannulation needle 40, the internal dilator 45, and the external dilator tip 33 provide a smooth, seamless surface without any gaps to prevent skin or other tissue jam to collect during cannulation. The external vascular dilator tip 33 may be blunt or rounded to stretch the opening created by the cannulation needle 40, without cutting or tearing the tissue. The external vascular dilator 30 also has funneled side orifices 32 to allow blood to enter the interior of the vascular dilator 30. The diameter of the vascular dilator 30 may be varied depending upon the blood flow rate desired for the procedure and the size of the vascular access.

A cannulation needle 40 with attached internal dilator 45 is guided through the arterial passageway 23 and vascular dilator 30 to cannulate a graft or fistula. The small bore adapter 22 can then be tightened around the cannulation needle 40 to prevent blood from exiting the arterial passageway 23 and securing the cannulation needle 40. Additionally, tightening the small bore adapter 22 is used to prevent undesired movement of the cannulation needle 40 during cannulation. Following perforation of the skin and wall of access by the cannulation needle 40, the internal dilator 45 followed by the external vascular dilator 30 is gently introduced into the fistula or graft. After securing the device, the cannulation needle 40 with attached internal dilator 45 is removed. A venous tube 50 has a narrow segment 51 with end opening 52 is then inserted into the venous passageway 21.

The venous tube narrow segment 51 is introduced through the venous passageway 21 through the external vascular dilator 30 and into the fistula or graft. The relatively small angle less than 30 degrees and preferably approximately 15 degrees between the venous and arterial passageways helps minimize the pressure drop and eliminate tube constriction at the bend. The venous tube narrow segment 51 is then advanced approximately 4 to 5-mm beyond the vascular dilator tip 33. As the venous tube 50 is freely rotatable within the body 10 and vascular dilator 30, the venous tube 50 may be turned to get through tortuous paths. Upon securing the venous tube with the large bore adapter 25, blood is then removed from the patient through the external vascular dilator side orifices 32 into the arterial passageway 23 and sent through the arterial tube 34 connected to the arterial passageway 23 for transfer to the hemodialysis machine. To achieve single access bi-directional flow, the patient's blood supply is then returned through the venous tube 50 and discharged through the side and end orifices into the patient's blood stream. Standard tubing clamps 55 may be used to prevent or limit blood flow when desired.

In its simplest embodiment, the vascular access device 10 can be used as a standalone procedure. In this case, the dialysis fistula or graft will be cannulated by a standard 15 gauge fistula needle. The vascular dilator 30 will be introduced over the standard dialysis needle, the needle will be removed and the vascular dilator 30 will be directly connected to the dialysis lines using standard connectors.

Additional features of specific embodiments are described in greater detail below.

Body

As shown in FIGS. 1-4, the body 20 may be a substantially rectangular cube shape, alternatively the body may have any shape suitable for containing the venous and arterial passageways and the appropriate angle alpha 24 between the passageways. For example, a V or Y-shaped fitting configuration would also be acceptable. The body 20 may be secured to the patient with removable Velcro strips, releasable adhesives, or attached with standard ties to the loops connected to the body of the device.

Vascular Dilator

The vascular dilator 30 size will preferably be between 6 and 16 french catheter sizes. The vascular dilator 30 has an interior conduit which alternately contains portions of the cannulation needle 40 with attached internal dilator 45 during cannulation and the narrow segment 51 of the venous tube 50 during blood transfer, thus serving as a sheath for portions of the cannulation needle 40, the internal dilator 45 and venous tube 50 within the patient's tissue. As such, when the cannulation is complete and the cannulation needle 40 and internal dilator 45 are removed, the resulting opening at the vascular dilator tip 33 within the external vascular dilator 30 would have at least twice the open area for blood flow that would be provided by the cannulation needle alone.

The external vascular dilator 30 preferably has a muzzle 31 to provide for attachment to the body 20 and a vascular dilator tip 33 with an open free end. The rim of the vascular dilator tip 33 may be beveled, blunt or rounded to prevent tissue damage when inserted into the vessel during regular cannulation.

The vascular dilator tip 33 in a beveled or rounded embodiment preferably has two or more vascular dilator funneled side orifices 32. This is to allow blood collection through the vascular dilator 30 during use even if the wall of the fistula or graft is sealing one of the openings. As such, it is preferable that the combined area of the vascular dilator side orifices 32 is greater than the area of the end opening of the vascular dilator tip 33. For vascular access with a high recirculation rate a vascular dilator 30 with side orifices located farther from the tip would be preferred. For a deeply located vascular access a longer external vascular dilator 30 may be used. Vascular dilator side funneled orifices 32 can have various geometric shapes. A round or oval configuration is preferred. With oval shaped orifices, to prevent extravasation of blood, the long axis would be perpendicular to the axis of dilator.

The vascular dilator side orifice 32 will preferably have a funneled shape narrowing from the outer surface of the vascular dilator 30 to its inner bore. Funneling of vascular dilator side orifice 32 will then provide additional space between the orifices and internal wall of the vessel vascular access. The distance of the vascular dilator side orifice 32 to the vascular dilator tip 33 is dependent upon the depth of the vascular access and recirculation rate for the particular vascular access. A dilator with a length greater than the standard length of 35 mm may be preferred to provide access in deeply located fistulas.

The vascular dilator tip 33 may be beveled at an acute angle to aid insertion through a tissue opening. The vascular dilator tip 33 may be either rounded or beveled at an acute angle to aid insertion through a tissue opening which will make it useful during buttonhole cannulation.

Unlike regular dialysis needles, it is safe to flip the vascular dilator 30 with or without flipping the body of the device without risk of damaging of endothelium as there are no sharp parts. Furthermore, it is provided that as the vascular dilator 30 is inserted through the cannulation, it will distend tissue of graft or fistula without causing additional trauma, bleeding or pain. To prevent post treatment bleeding at least a portion of the vascular dilator 30 residing in the sub epidermal layer of the skin may be covered with a local hemostatic. Other medicants that may be used, as for example, a coating include medical lubricants, anesthetics, anti-microbials, disinfectants or anti-clotting agents.

Cannulation Needle

The cannulation needle 40 is preferably a standard hollow 15 to 18-gauge aspirator needle approximately 4-mm in length, with a razor sharp tip 42 for making the cannulation. The cannulation needle 40 may have 3 or more bevels along its length. Using a smaller diameter cannulation needle helps to reduce patient pain and to reduce damage to graft or fistula as the cannulation needle tip 42 passes through tissue such as skin and the blood vessel wall. The internal dilator 45 with the cannulation needle 40 is substantially the same diameter as the vascular dilator tip opening diameter to prevent tissue from entering the vascular dilator 30 or from gaps between the external vascular dilator 30, the internal dilator 45 or the cannulation needle 40 during cannulation and dilation.

Venous Tube

Venus tube 50 shown in FIG. 7D is composed of flexible tubing for inserting through the venous passageway 21 and into the vascular dilator 30 following removal of the cannulation needle 40. The venous tube 50 carries blood from the patient through the vascular dilator 30, body 20, venous passageway 21 and large bore adapter 25. The venous tube 50 includes a narrow segment 51 which has sufficient rigidity for insertion into the graft or fistula. The narrow segment 51 may have a 0.1 to 0.3 mm wall thickness. A large interior internal diameter narrow segment 51 is preferred. In one embodiment, an internal diameter of 1.8 mm and a wall thickness of approximately 0.1 mm may be used to minimize pressure drop in venous segment of the system, which is contributing factor in developing of stenosis of hemodialysis access. A wall thickness of 0.1 mm is preferred. The venous tube tip 52 may include a strip of metal or other radio opaque material to assist identifying the location of within the graft or fistula during insertion using common medical imaging methods. The annular space between the inner surface of the vascular dilator 30 and the external surface of venous tube tip 52 forms a conduit for blood flow into the body 20 and to the arterial tube 34.

Blood Flow Detector

Figure 8:
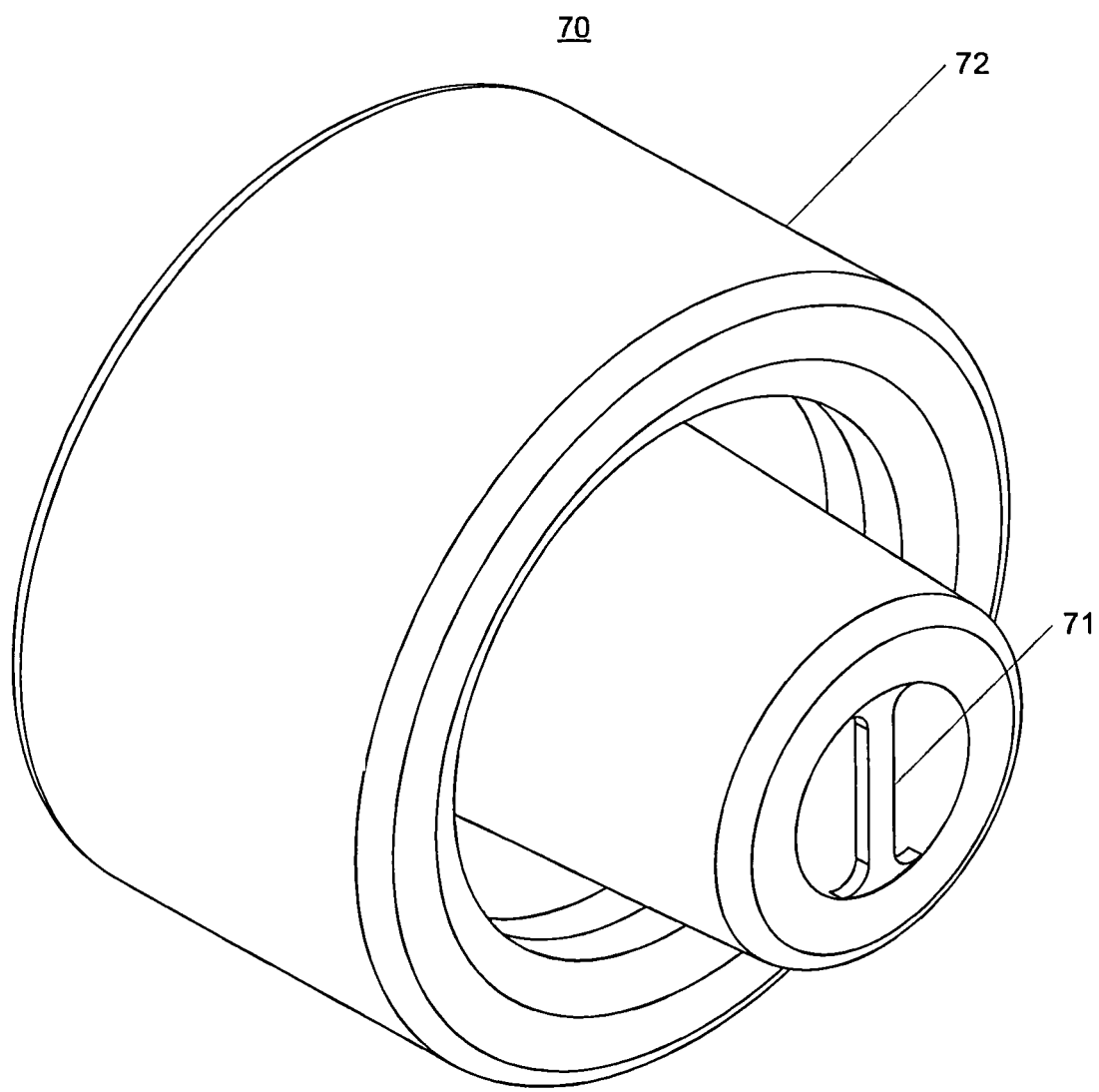
FIG. 8 provides a perspective view of blood flow detector.

To assist medical personnel during cannulation, the vascular access device 10 may optionally include a blood flow detector 70, shown in FIG. 8, that will inform the technician when a successful cannulation has been made. The disclosed blood flow detector 70 includes a frame 72 and a vibrator 71 and relies on the patient's natural blood pressure to operate. The frame 72 containing a vibrator 71 is attached to the cannulation needle 40. The vibrator may provide an audible signal such as a whistle, if a rubber membrane is used, or a visual signal if, for example a flap valve is used. As the needle punctures a graft or fistula, blood, taking the path of least resistance, enters the cannulation needle 40. The blood displaces air in the cannulation needle 40, which activates the vibrator 71 providing an indication that the cannulation has been completed.

Figure 9A:
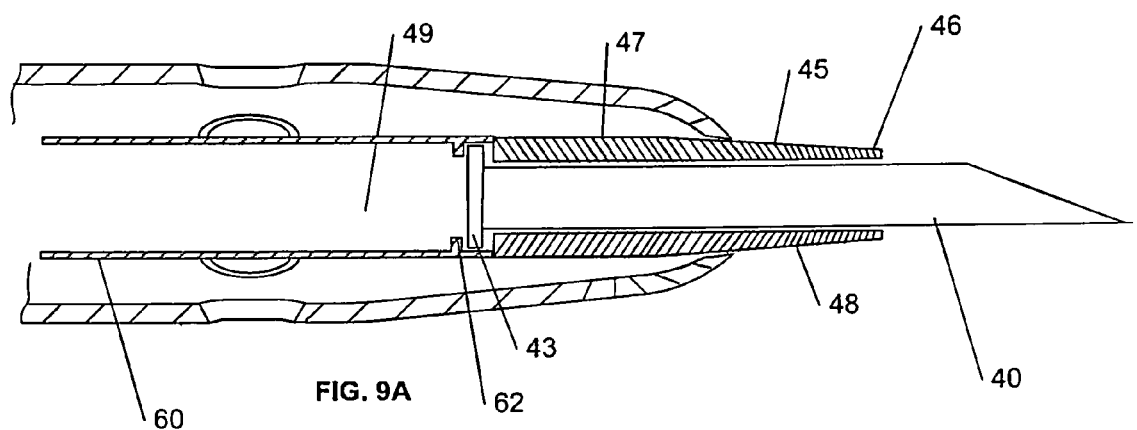
FIG. 9A provides a cross sectional view of an embodiment of a vascular dilator with an internal dilator.

In the embodiment as shown in FIG. 9A, a second cone shaped dilator or internal dilator 45 is attached to or integral with the cannulation needle 40. The internal dilator 45 may be removably attached to an internal dilator extension 60. In this embodiment, the internal dilator 45 having a tip end 46 and a base end 47 will have a length approximately between 3 to 4-mm and ending inside the arterial passageway 23 inside external vascular dilator 30. Along its longitudinal axis, the internal dilator 45 includes an inner bore 49 containing the cannulation needle 40. The cannulation needle 40 may have a stop 62 to secure the needle flange 43 within the internal dilator 45. The inner bore 49, may be removable from or fixed to the cannulation needle 40, but is of a diameter and characteristic sized to prevent slippage along the cannulation needle 40 during use. The internal dilator 45 may include a tapered segment 48, forming a tapered cone between the base end 47 and the tip end 46. The base end 47 may also include a cylindrical portion adjacent to the tapered segment 48. Including an internal dilator 45 results in increasing the diameter of the access front opening of the external vascular dilator tip 33 while minimizing trauma to the access point. Depending on the cannulation needle 40 the internal dilator's tip end 46 diameter will be between approximately 1.27 mm for a 18 gauge needle to approximately 1.83 mm for a 15 gauge needle. The diameter of the base end 47 will be less or equal than the front opening of the external vascular dilator tip 33 or less then internal diameter of vascular dilator 30 which in an embodiment may range from 8 french size to 16 french size. The tip end 46 located at or near the bevel of the internal dilator 45 will have a have a diameter to provide a smooth transition from the needle to the internal dilator 45 to the external vascular dilator 30 resulting in a smoother/less traumatic dilation of tissues along the cannulation track. The internal dilator 45 is preferably made from a low friction coefficient material (for example, Delrin® or 316L stainless steel) to decrease insertion force and/or coated with biocompatible lubricant.

Figure 9B:
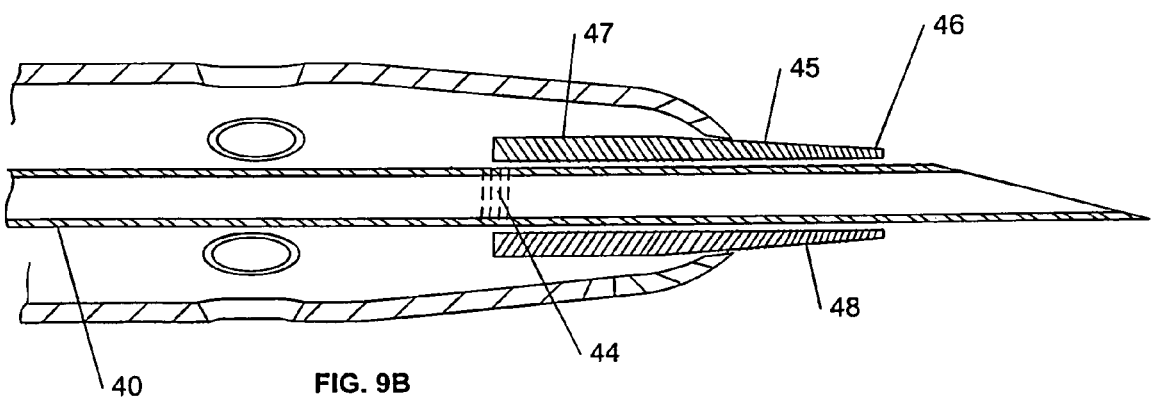
FIG. 9B provides a cross sectional view of another embodiment of a vascular dilator with an internal dilator.

In another embodiment as shown in FIG. 9B, the cannulation needle 40 may be constructed as two separate sections. Using for example, a threaded connection, these sections may separate into a distal section and a proximal section with a needle joint 44 to connect the needle sections. Cannulation needle 40 can be removably attached to the base end 47 of the internal dilator 40. This design lends itself to including disposable elements. Particularly for disposable elements, polymer tubing may be used for this device. Optimally Pebax® 72 D tubes with ultrathin walls with OD 2.0 mm and ID 1.85 mm are preferred for use in the device for the venous tube 50. For an external vascular dilator 30, preferred materials include SS 316L with ultrathin walls. For the internal dilator 45 either Delrin® or SS 316L may be used.

The internal dilator 45 may be integral with at least a portion of the cannulation needle 40 and insertion would proceed until the tapered segment 48 sealing engaged the opening of the vascular dilator tip 33, forming a seal between the cannulation needle 40 and the vascular dilator 30. The vascular dilator 30 is then inserted until at least a portion is within the vascular access. In the present invention, the small bore adapter 22 would not use the standard Luer connectors which typically connect vascular access device to hemodialysis lines, often having an ID of no more than 3.5 mm. In a preferred embodiment vascular access device larger size connectors with an ID of not less than 4.5 mm are used to avoid excessive pressure drop and the resulting will minimizing of flow rate which nullify the benefits of the device from using smaller diameter cannulation needles.

An internal dilator 45 can provide improved functionality for vascular access. The internal dilator 45 provides a smoother tapered off transition between the cannulation needle 40 and the vascular dilator 30. This provides for a less traumatic cannulation, less painful and resulting in a more gentle distension of tissues during the cannulation process. Using this "Russian Doll" procedural approach, after the removal of the cannulation needle 40 with internal dilator 45, a vascular dilator 30 having a cannulation needle tip 42 having a front opening larger than the diameter of the cannulation needle 40. This allows the use of a larger diameter venous tube tip 52 without using a larger size cannulation needle 40.

In the present invention in addition to access through a fistula or graft, other access techniques used in two-needle procedures may be utilized to increased advantage with the present invention. For example, the buttonhole technique and the Z Track Technique are used for access and have been evaluated with respect to the present invention.

With the buttonhole technique, a needle is inserted into the same site, at the same angle for every cannulation. As such, a distinct path is created for the cannulation needle to follow for each access removing the need to utilize a new access site for each treatment.

Histological evaluation of a buttonhole track obtained using the present invention has been performed. The available prior art regarding the histological examination of cannulation track in buttonhole technique was reviewed. It was found that the expected data would show connective tissue variation in different degree of maturation. The evaluation of the present invention, had the unexpected finding of sclerotic changes of vessel adventitia in the tissue.

The Z Track Technique has been used for decades to decrease bleeding time and infection rate after cannulation. The tissue to be injected is pulled in the direction of the body's midline. It is held in this position during the time and after the drug is injected. When the tissue is released, the usually straight needle track will become a broken line similar to the letter Z. This holds the medication deep in the muscle and prevents upward seepage through the tissues along the needle track.

A unique modification of this technique which takes advantage of unique characteristics of the present invention, utilizing the Z Track Technique in consideration of Langer's lines. Langer's lines, sometimes called cleavage lines, correspond to the natural orientation of collagen fibers in the dermis, and are generally parallel to the orientation of the underlying muscle fibers. With the present invention, it has been determined that if the skin is stretched parallel to Langer line in area of cannulation, a significant decrease in post treatment bleeding time and a decrease in insertion force was found. Table 1 provides the results for animal testing conducted using embodiments of the vascular access device having the vascular dilator, with and without the internal dilator.

With distance between side-holes and tip of internal tube between 4.5-7 mm and blood flow rate inside access we are achieving recirculation rate about 0.2-3.2% by spectrophotometry during bench trial and 0% by ultrasonic during animal trial. As such, the device very useful for stenotic, angled and other vascular accesses with challenging geometry.

TABLE 1

Animal Trial Results - Multilayered (Double) dilator

| Needle size/ type/no of trials* | Insertion force (newtons) | Post treatment bleeding time (minutes) | Blood lost (ml) | Discomfort level** (0-10 scale) | Flow rate (ml/min) | Pressure Range (mm Hg) arterial/venous |
|---|---|---|---|---|---|---|
| 18 gauge sharp needle + double 9french dilator/95 | 29-35 | one-five | one-three | 0-2 | 500-650 | −120-140/140-160 |
| 17 g sharp + double 9french dilator/100 | 26-28 | Three-five | One-three | 0-2 | 500-650 | −120-140/140-160 |
| 16 g sharp + double 9french dilator/96 | 22-27 | Four-six | three-five | 0-1 | 550-650 | −120-140/140-160 |
| 15 g sharp + double 9french dilator/100 | 20-25 | Ten-twelve | Five-fifteen | 0-3 | 550-650 | −120-140/140-160 |
| 18 g buttonhole + 9double french dilator/60 | 32-35 | Three-five | One-three | 0 | 500-600 | −120-140/140-160 |

TABLE 1-continued

Animal Trial Results - Multilayered (Double) dilator

| Needle size/ type/no of trials* | Insertion force (newtons) | Post treatment bleeding time (minutes) | Blood lost (ml) | Discomfort level** (0-10 scale) | Flow rate (ml/min) | Pressure Range (mm Hg) arterial/venous |
|---|---|---|---|---|---|---|
| 16 g buttonhole + 9double french dilator/65 | 31-32 | Three-five | One-three | 0-1 | 500-650 | −120-140/140-160 |
| 15 g buttonhole + 9double french dilator/60 | 27-30 | Three-five | One-three | 0-1 | 550-650 | −120-140/140-160 |

TABLE 2

Animal Trial Results - Single Dilator

| 18 g sharp + single 9french dilator/95 | 40-47 | one-five | one-three | One-two | 180-220 | −110-140/250-320 |
|---|---|---|---|---|---|---|
| 17 g sharp + single 9french dilator/100 | 39-44 | Three-five | One-three | One-three | 180-220 | −110-140/250-320 |
| 16 g sharp + single 9french dilator/95 | 34-37 | Four-six | three-five | One-four | 180-220 | −110-140/250-320 |
| 15 g sharp + single 9 french dilator/90 | 32-35 | Ten-twelve | Five-fifteen | Two-five | 180-220 | −110-140/250-320 |
| 18 g buttonhole + 9 single french dilator/62 | 39-47 | Three-five | One-three | 0 | 180-220 | −110-140/250-320 |
| 16 g buttonhole + 9single french dilator/65 | 34-40 | Three-five | One-three | 0-1 | 180-220 | −110-140/250-320 |
| 15 g buttonhole + 9single french dilator/60 | 32-35 | Three-five | One-three | 0-1 | 180-220 | −110-140/250-320 |

*three pigs used for each test with radiocephalic fistula
**amount/amplitude of pig's tail movement during cannulation
***arterial passageway of device/venous passageway of device As shown in Table 1, minimizing post bleeding time was achieved by creating small cannulation track (cannulation performed by small size needle) with following compression of vessels inside cannulation track by inserting of large size of dilator for 4 hours.

TABLE 3

Cannulation Needle Size for Various Blood Flow Rates (BFR)

| Needle Gauge | Prior Art Device* (ml/min) | Multilayer Dilator** (ml/min) |
|---|---|---|
| 17 | <300 | 500-650 |
| 16 | 300-350 | 550-650 |
| 15 | 350-450 | 550-650 |
| 14 | >450 | |

Source:
*National CMS Fistula First Project
**Table 1 above

As summarized in Table 3, the multilayer vascular dilator can achieve very high blood flow rates with a narrow gauge cannulation needle.

The invention claimed is:
1. A method to facilitate bi-directional flow during dialysis through a single vascular access point comprising:

providing a vascular access device, wherein the vascular access device includes a body, a first dilator, a second dilator, and a cannulation needle, wherein the vascular access device's body has a first passageway and a second passageway, wherein the second dilator is in fluid communication with the first passageway, wherein the first dilator is positioned inside the second dilator, and wherein the cannulation needle is positioned inside the first dilator;

using a modified Z track technique, cannulating a wall of a blood vessel of a patient at the vascular access point with the cannulation needle to access blood in the patient's blood vessel, wherein the modified Z track technique includes pulling skin in a direction parallel to a Langer line in an area of the cannulating;

urging the first dilator into the patient's blood vessel;

urging the second dilator, which surrounds the first dilator, into the patient's blood vessel;

withdrawing the cannulation needle and the first dilator from the patient's blood vessel and removing the cannulation needle and the first dilator from the second dilator;

threading a blood-conveying tube through the second passageway of the vascular access device's body and through the second dilator and into the patient's blood vessel; and removing blood for a blood dialysis unit through the second dilator and returning the blood from the blood dialysis unit through the blood-conveying tube.

2. The method of claim 1, wherein the first dilator and the second dilator are consecutively passed through the vascular access point.

3. The method of claim 1, wherein the cannulating of the wall of the blood vessel forms a cannulation track, and wherein the second dilator compresses the cannulation track from inside the wall of the vessel and skin above the access point in order to minimize bleeding.

4. The method of claim 1, wherein the cannulating includes performing a buttonhole technique in order to produce sclerotic changes of vessel adventitia in the tissue.

5. The method of claim 1, wherein the second dilator includes a free end forming a second dilator tip, and wherein the second dilator tip includes a plurality of second dilator side orifices.

6. The method of claim 1, wherein the second dilator includes a free end forming a second dilator tip, wherein the second dilator tip includes a plurality of second dilator side orifices, and wherein at least one of the plurality of second dilator side orifices has a funnel shape that is wider at its outer edge than at its inner edge.

7. The method of claim 1, wherein the second dilator includes a free end forming a second dilator tip, wherein the second dilator tip includes a plurality of second dilator side orifices, wherein the second dilator tip also has an end opening, and wherein an area of the plurality of second dilator side orifices is greater than an area of the end opening.

8. The method of claim 1, further comprising:
attaching a blood-flow detector to the cannulation needle, wherein the blood-flow detector includes a vibrator attached to a frame of the blood-flow detector; and
detecting, using activation of the vibrator in the blood-flow detector, blood flow into the cannulation needle during the cannulating.

9. The method of claim 1, wherein the second passageway and the first passageway intersect at an angle in the range of 5 degrees to 30 degrees.

10. A method for accessing a dialysis site of a patient comprising:
providing a first dilator, a second dilator, and a cannulation needle;
placing the cannulation needle within the first dilator;
inserting the first dilator with the cannulation needle into the second dilator;
using a modified Z track technique, cannulating a dialysis site with the cannulation needle, wherein the modified Z track technique includes pulling skin in a direction parallel to a Langer line in an area of the cannulating;
urging the first dilator into the dialysis site having fluid communication with a blood supply of the patient;
urging the second dilator into the dialysis site having fluid communication with the blood supply;
removing the cannulation needle and the first dilator from the dialysis site; and
connecting the second dilator to a dialysis line to provide blood to a blood dialysis unit.

11. The method of claim 10, wherein the first dilator and the second dilator are consecutively passed into the dialysis site.

12. The method of claim 10, wherein the dialysis site includes a blood vessel, wherein the cannulating of the dialysis site forms a cannulation track, and wherein the second dilator compresses the cannulation track from inside a wall of the blood vessel in order to minimize bleeding.

13. The method of claim 10, wherein the cannulating includes performing a buttonhole technique in order to produce sclerotic changes of vessel adventitia in the tissue.

14. The method of claim 10, wherein the second dilator includes a free end forming a second dilator tip, and wherein the second dilator tip includes a plurality of second dilator side orifices.

15. The method of claim 10, wherein the second dilator includes a free end forming a second dilator tip, wherein the second dilator tip includes a plurality of second dilator side orifices, and wherein at least one of the plurality of second dilator side orifices has a funnel shape that is wider at its outer edge than at its inner edge.

16. The method of claim 10, wherein the second dilator includes a free end forming a second dilator tip, wherein the second dilator tip includes a plurality of second dilator side orifices, wherein the second dilator tip also has an end opening, and wherein an area of the plurality of second dilator side orifices is greater than an area of the end opening.

17. The method of claim 10, further comprising:
attaching a blood-flow detector to the cannulation needle; and
detecting, using the blood-flow detector, blood flow into the cannulation needle during the cannulating.

18. The method of claim 10, wherein the cannulating of the dialysis site, the urging of the first dilator, and the urging of the second dilator are each performed with an insertion force not greater than 35 Newtons.

19. The method of claim 10, wherein the method provides a post-treatment bleeding time of less than five (5) minutes.

20. The method of claim 10, wherein the method provides a post-treatment blood loss of less than 5 milliliters (ml).

* * * * *